ބ
United States Patent [19]

Montal et al.

[11] Patent Number: 5,837,265
[45] Date of Patent: Nov. 17, 1998

[54] CHEMICALLY-MODIFIED CLOSTRIDIATOXIN WITH IMPROVED PROPERTIES

[75] Inventors: Mauricio Montal; Antonio Ferrer-Montiel, both of La Jolla, Calif.

[73] Assignee: The Regents of the University of California, Oakland, Calif.

[21] Appl. No.: 612,571

[22] Filed: Mar. 8, 1996

[51] Int. Cl.$^6$ .......................... A61K 39/00; A61K 39/02; A61K 39/06

[52] U.S. Cl. .......................... 424/239.1; 514/2; 532/324; 424/832

[58] Field of Search .............................. 424/236.1, 239.1, 424/247.1; 435/193, 194; 514/2

[56] References Cited

PUBLICATIONS

Database Medline, US National Library of Medicine (Bethesda, MD), No. 82046912, Shibaeva, et al., "Changes in Biological Properties of Botulinum Neurotoxin A Induced by Chemical Modification of its Molecule . . . ".

Database Embase, Elsevier Sci. B.V., No. 74056271, Stein, et al., "Modification of Tetanus Toxin with Selective Chemical Reagents," Abstract Z, Immunitatsforsch. Exp. Immun., 1973, vol. 145, No. 5.

Database Medline, US National Library of Medicine (Bethesda, MD), No. 89261699, M. Woody et al., "Effects of Tetranitromethane on the Biological Activities of Botulinum Neurotixin Types A, B and E", Abstract.

Nagahama, et al., "Effect of prior treatment with Clostridium perfringens epsilon toxin inactivated by various agents on lethal, pressor and contractile activities . . . ", FEMS Microbiology Letters 72 (1990) 59–62.

Robinson, et al., "Tetanus Toxin, The Effect of Chemical Modifications on Toxicity, Immunogenicity, and Conformation," Journal of Biological Chemistry, vol. 250, No. 18, pp. 7435–7442, Sep. 25, 1975.

Ferrer–Montiel, et al., "Tyrosine Phosphorylation Modulates the Activity of Clostridial Neurotoxins," Journal of Biological Chemistry, vol. 271, No. 31, pp. 18322–18325, Aug. 2, 1996.

Pernollet, et al., "OH Treatment of Tetanus Toxin Reduced its Susceptibility to Limited Proteolysis with More Efficient Presentation to . . . ", Molecular Immunology, vol. 30, No. 18, pp. 1639–1646, 1993.

Chemical Abstracts, vol. 80, 1974, p. 307, col. 2, abstract No. 25783x, Bizzini et al., "Immunochemistry of Tetanus Toxin. Nitration of Tyrosyl Residues in Tetanus Toxin.", Eur. J. Biochem., 1973, vol. 39, No. 1.

Sakurai et al., "The Inactivation of Clostridium Perfringens Epsilon Toxin by Treatment with Tetranitromethane and N–Acetylimidazole," Toxicon, vol. 25, No. 3, pp. 279–284, 1987.

Woody et al. Effect of tetranitromethane on biological activities of botulinum neurotoxin types A,B, and E. Mol. Cell. Biochemistry, 85:159–169, Jan. 1989.

*Primary Examiner*—Cecilia J. Tsang
*Assistant Examiner*—Michael Borin
*Attorney, Agent, or Firm*—Fish & Richardson P.C.

[57] ABSTRACT

The invention consists of modified Clostridium neurotoxin compounds, pharmaceutical compositions containing such compounds and methods for preparing such compounds. In particular, the compounds of the invention are purified *Clostridium botulinum* and *Clostridium tetani* neurotoxins in which the tyrosine residues have been modified to have a negative charge (e.g., by covalent attachment of a phosphate or sulphate thereto) or in which the tyrosine residues have been substituted with amino acids having a negative charge (e.g., glutamate, aspartate, or negatively charged, non-natural amino acids). Toxins having phosphorylated tyrosine residues in both the light and heavy chains of the toxins are preferred. Methods for enzymatic and chemical modification of tyrosine residues in purified Clostridium neurotoxins are provided.

16 Claims, 6 Drawing Sheets

CHEMICALLY-MODIFIED CLOSTRIDIATOXIN WITH IMPROVED PROPERTIES

STATEMENT OF FEDERALLY SUPPORTED RESEARCH

The development of this invention was supported by funds provided by the U.S. Department of the Army, Medical Research Command, under Grant No. DAMD-17-93-C-3100. The Government may have certain rights to this invention.

BACKGROUND OF THE INVENTION

1. Field of the Invention

The invention relates to pharmacologically active compositions of neurotoxins obtained from *Clostridium botulinum* and *Clostridium tetani*. Methods for producing the compositions of the invention are also provided.

2. History of the Invention and Prior Art

The neurotoxin serotypes produced by *Clostridium botulinum* (collectively, BoTx) are some of the most potent neuroparalytic agents known to man and are the causative agents for botulism. Paradoxically, BoTx serotype A (BoTxA) is also considered to be an effective pharmaceutical agent for use in the treatment of certain neuromuscular disorders associated with uncontrolled muscle contractions or spasms such as disorders of the extraocular muscles (e.g., strabismus and nystagmus) as well as dystonias (involuntary contractions of facial, hand and neck muscles) (see, e.g., *The New England Journal of Medicine*, 324:1186–1194, 1991).

More recently, BoTxA has been approved for use in temporarily smoothing facial wrinkles. BoTxA is believed to produce a reversible, nondegenerative flaccid paralysis of mammalian skeletal muscle, presumably by blocking the exocytosis of acetylcholine at peripheral, presynaptic cholinergic terminals, with limited activity at synapses in the central nervous system (Rabasseda, et al., *Toxicon*, 26:329–326, 1988).

Other serotypes of BoTx have been identified that have immunologically distinct phenotypes; i.e., serotypes B, C1, C2, D, E, F and G (Simpson, et al., *Pharmacol.Rev.*, 33:155–188, 1981). All of the BoTx serotypes are believed to be proteins of about 150 kDa molecular weight that are comprised of two polypeptide chains linked by disulphide bridges. The shorter of the two chains (the light chain, LC) is believed to be responsible for the toxicity of the toxin, while the longer of the two chains (the heavy chain, HC) is believed to be responsible for the penetration of the toxin into nervous tissue. Although antigenically different to some extent, the Botulinum serotypes are believed to be similar in their pharmacological actions (Brin, et al., "Report of the Therapeutics and Technology Assessment Subcommittee of the American Academy of Neurology", *Neurology*, 40:1332–1336, 1990). For example, each of the serotypes cleaves cellular protein substrates which are involved in the release of the acetylcholine neurotransmitter into the synaptic cleft of neurons in the peripheral cholingergic nervous system. Protein substrates for BoTx include SNAP-25 (synaptosome-associated protein, cleaved by the A and E serotypes), syntaxin (cleaved by the C serotype) and synaptobrevin (cleaved by the B, D, F and G serotypes).

The tetanus toxin produced by *Clostridium tetani* (TeTx) is believed to share substantially the same mode of action of BoTx; i.e., TeTx acts as an anticholinergic, presynaptic neurotoxin. Serotypes A and E of the BoTx share a substantial degree of sequence homology with TeTx (DasGupta, et al., *Biochemie*, 71:1193–1200, 1989). Further, although TeTx primarily acts on the central (rather than peripheral) nervous system to produce rigid (rather than flaccid) muscle paralysis, at least one peptide digestion fragment of TeTx (fragment Ibc) has been shown to act peripherally to produce flaccid paralysis in a manner similar to BoTx (Fedinic, et al., *Boll. Ist. Sieroter Milan*, 64:35–41, 1985; and, Gawade, et al., *Brain Res.*, 334:139–46, 1985). TeTx cleaves synaptobrevin.

TeTx and most BoTx serotypes are available from commercial sources. However, as presently manufactured, up to 90% of the active toxin may be lost during purification to a pharmacologically useful product, resulting in a composition comprised of a combination of active and inactive toxin. Typically, a pharmacological purified toxin composition is lyophilized for storage, then reconstituted for clinical use with saline or another pharmaceutically acceptable carrier (see, e.g., the manufacturing and lyophilization process described in published European Patent Application No. 0 593 176 A2 [process for limiting the volume of inactive toxin in a purified BoTxA composition]). Once reconstituted, the presently available toxin compositions are typically unstable and quickly lose potency at room temperature. Moreover, even when used soon after reconstitution, the relatively low active toxin concentrations present in commercially available toxin compositions limit the activity of each dose, thereby requiring that the toxin be administered repeatedly over a course of time at the same point of entry into tissue.

A need, therefore, exists for pharmaceutically acceptable BoTx and TeTx compounds which have greater thermal stability and proteolytic activity than do currently available toxin compositions.

SUMMARY OF THE INVENTION

The invention comprises BoTx and TeTx compounds having enhanced proteolytic activity and thermal stability as compared to toxins obtained and purified by conventional techniques. Methods and reagents for use in preparing the toxin compositions of the invention are also provided.

Specifically, the invention provides pharmaceutically acceptable compositions of all BoTx serotypes, as well as TeTx compositions. In each composition, tyrosine residues in at least the LC and, preferably, in both the LC and HC of the toxin present are phosphorylated or sulfated to provide a negative charge to each modified tyrosine. Alternatively, tyrosine residues in the toxins are substituted with negatively charged amino acids (e.g., glutamate, aspartate, or negatively charged non-natural amino acids). Both L- and D-isomers of each toxin are provided by the invention. The enhancement of activity and stability of the inventive toxin compositions as compared to presently available toxin compositions is illustrated by comparison between fully phosphorylated BoTxA to BoTxA obtained and purified by conventional techniques; i.e., unphosphorylated BoTxA.

On contact with a BoTxA substrate (SNAP-25), the substrate is cleaved by a 10 nanomolar concentration of phosphorylated toxin in about 5 minutes. In contrast, at even a 50 nanomolar concentration, cleavage of the substrate is not achieved by the unphosphorylated toxin until after 30 minutes or more of contact. Further, at a temperature of 37° C., the unphosphorylated toxin becomes virtually inactivated within about 2 hours, while the phosphorylated toxin retains 50% or more of its proteolytic activity for up to 10 hours at the same temperature. Thus, modification of the toxin to provide it with a negative charge enhances the proteolytic activity and thermal stability of the toxin.

The invention also provides methods for producing BoTx and TeTx compounds modified according to the invention using either enzymatic or non-enzymatic (chemical) reagents. Pharmaceutical compositions containing such compounds are also provided.

BRIEF DESCRIPTION OF THE DRAWINGS

FIGS. 5(a–b) are graphs depicting the rate of cleavage of SNAP-25 by pp60$^{src}$ phosphorylated BoTxA (closed squares) and unphosphorylated BoTxA (closed circles). Panel A depicts rate of cleavage as a function of toxin concentration, while panel B depicts rate of cleavage as a function of time.

FIGS. 6(a–b) are graphs depicting the rate of cleavage of SNAP-25 by pp60$^{src}$ phosphorylated BoTxE (closed squares) and unphosphorylated BoTxE (closed circles). Panel A depicts rate of cleavage as a function of toxin concentration, while panel B depicts rate of cleavage as a function of time.

FIGS. 8(a–b) are graphs depicting the rate of cleavage of SNAP-25 by pp60$^{src}$ phosphorylated BoTxA (closed squares) and unphosphorylated BoTxA (closed circles), wherein the unphosphorylated starting BoTxA materials were inactivated (to a loss of approximately 90% activity) at 37° C. for 6 hours before phosphorylation of one-half of the materials and incubation with SNAP-25.

DESCRIPTION OF THE PREFERRED EMBODIMENTS

I. METHODS FOR PRODUCING NEGATIVELY CHARGED, TYROSINE MODIFIED BoTx AND TeTx
A. Unphosphorylated BoTx and TeTx Starting Materials Unphosphorylated TeTx and known serotypes of BoTx for use as starting materials to produce the toxin compositions of the invention may be purified to homogeneity using techniques which will be known to, or can be readily ascertained by, those of ordinary skill in the art. For reference in this regard, descriptions of each purified BoTx serotype are provided in Shone, *Clostridium botulinum* neurotoxins, their structures and modes of action, "Natural Toxicants in Foods" (Horwood, 1987) at pp 11–57. The manufacturing method utilized in producing a commercial BoTxA product supplied by the United Kingdom firm Porton under the tradename DYSPORT™ is set forth at Hambleton, *J.Neurol.*, 239:16–20 (1992); in addition, a related isolation and purification technique is described in Hambleton, et al., Production, purification and toxoiding of *Clostridium botulinum* type A toxin, "Biomedical Aspects of Botulism" (Acad. Press, 1981) at pp 247–260. Reported amino acid sequences and structural characteristics for the BoTx and TeTx toxins can also be found at, for example, Eisel, et al., *EMBO J.*, 5:2495–2502, 1986; Hambleton, et al., Botulinum toxin structure, action and clinical uses, "Neurotoxins and Their Pharmacological Implications" (Raven Press, 1987) at pp. 233–260 [BoTx toxins]; Thompson, et al.,*EurJ.Biochem.*, 189:73–81, 1990 [BoTxA; nucleotide sequence for the encoding gene included]; Montal, et al., *FEBS Lett.*, 313:12–18, 1992 [TeTx and BoTx channel forming motifs]; DasGupta and Sugiyama, *Biochem.Biophys.Res.Comm.*, 48:108–112, 1972 [subunit structure common to BoTx serotypes A, B and E]. A method useful in producing lyophilized BoTxA is also described in published EPO Application No. 0 593 176 A2. The disclosures of these references are each incorporated herein by this reference for the sole purpose of illustrating the state of knowledge in the art regarding the isolation and purification of BoTx and TeTx. The products of each isolation and purification technique known in the art are unphosphorylated toxins.

With reference to the known structural characteristics of BoTx and TeTx, conventional techniques for isolation and purification of proteins may be used (in addition to the particular methods referred to in the references cited above) to obtain substantially pure unphosphorylated toxin starting materials useful in producing the toxin compounds of the invention. Briefly, substantially pure BoTx or TeTx may be obtained through microbial expression, by synthesis, or by purification means known to those skilled in the art, such as affinity chromatography. In this regard, the term "substantially pure", as used herein denotes a protein which is substantially free of other compounds with which it may normally be associated in vivo. In the context of the invention, the term refers to homogenous toxin, which homogenicity is determined by reference to purity standards known to those of ordinary skill in the art (e.g., purity sufficient to allow the N-terminal amino acid sequence of the protein to be obtained).

BoTx and TeTx peptides can be synthesized by such commonly used methods as t-BOC or Fmoc protection of alpha-amino groups. Both methods involve stepwise syntheses whereby a single amino acid is added at each step starting from the C terminus of the peptide (see, Coligan, et al., *Current Protocols in Immunology*, Wiley Interscience, 1991, Unit 9). Peptides of the invention can also be synthesized by various well known solid phase peptide synthesis methods, such as those described by Merrifield (*J. Am. Chem Soc.*, 85:2149, 1962), and Stewart and Young (*Solid Phase Peptides Synthesis*, Freeman, San Francisco, 1969, pp 27–62), using a copoly (styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on a "SEPHADEX G-15" or "SEPHAROSE" affinity column. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Additionally, unphosphorylated BoTx and TeTx toxin preparations may be obtained from commercial sources. Examples of such sources and their respective products include BoTxA preparations supplied by Allergan, Inc. of Irvine, Calif. under the tradename "BOTOX" and by Porton Products Ltd, of the United Kingdom under the tradename "DYSPORT". A pentavalent toxoid of all eight known Botulinum serotypes is also available as an investigational drug from the U.S. Center for Disease Control in Atlanta, Ga. Preparations of individual BoTx serotypes are also available from Wacko of Tokyo, Japan. Of the individual BoTx serotype preparations, BoTxA preparations are currently the most preferred for their known safety and efficacy. Tetanus toxins for use as vaccines are also commercially available from, for example, Lederle Laboratories of Wayne, N.J. under the tradename "TETANUS TOXOID PUROGENATED" as well as from Sigma Chemical of St. Louis, Mo. and Calbiochem of San Diego, Calif.

B. Phosphorylation of BoTx and TeTx

For convenience, this disclosure will refer primarily to the preferred embodiment of the invention wherein tyrosine residues in a BoTx or TeTx compound are phosphorylated. However, while the invention is not limited by any particular theory concerning the mechanism by which the proteolytic activity and thermal stability of the toxins is enhanced, phosphorylation of the tyrosine residues results in a shift in the charge of the toxin product from neutral to negative. Thus, those of ordinary skill in the art will appreciate that other modifications of the toxin which produce a shift in the toxin to a negative charge ("negatively charged" toxin) at sites where tyrosine residues are present in the unmodified toxin would also be expected to enhance the activity and stability of the toxin, including sulfation of the tyrosine residues (by covalent attachment of a sulphate to the hydroxy group of tyrosine residues in the toxin) or substitution of all or a portion of the residues with negatively charged residues (e.g., aspartate, glutamate, or non-naturally occurring, negatively charged amino acids). So modified, such negatively charged toxins are regarded for purposes of this disclosure as having "charge-modified" tyrosine residues. In other words, the term "charge-modified tyrosine residues" shall refer to both negatively charged tyrosine residues (prepared according to the invention) and toxins wherein tyrosine residues have been substituted with glutamate, aspartate, or non-naturally occurring amino acids having a negative charge.

In the latter respect, it is well recognized that L-bond peptides are susceptible to proteolytic degradation, restricting their application as drugs. However, this obstacle has been successfully bypassed in some cases by synthesizing analogues which contain D-bond amino acids or non-natural amino acids. The addition of a single D-amino acid at the C-terminal position is enough to enhance the resistance to proteolytic degradation by exopeptidases, without significantly altering the secondary structure of the peptide [Abiko, supra]. Resistance to endopeptidases can be achieved by including individual non-cleavable non-peptidic bonds in points in the peptide sequence that are specially sensitive to enzymatic degradation [Meyer, et al., *J. Med. Chem.* 38:3462–3468 (1995); Guichard, et al., *Peptide Research* 7:308–321 (1994)]. Reverse amide bonds Ψ[NHCO], reduced amide bonds Ψ[CH$_2$NH] or retro-reduced bonds Ψ[NHCH$_2$] can be used as surrogates of the amide link [CONH] in ESUPs of the invention. Reduced amide links are preferred, since they result only in minor destabilisation of α-helices [Dauber-Osguthorpe, et al., *Int. J. Pep. Prot. Res.* 38:357–377 (1991)]. Thus, the invention includes BoTx and TeTx modified to substitute negatively charged, non-natural amino acids for tyrosine residues in the toxins.

Additionally, charge-modified toxins of the invention can be synthesized in all-D-conformations. All-D-peptides can be equally active as the original all-L-peptides [Merrifield, et al., *Ciba Foundation Symposium* 186:5–20 (1994); Wade, et al., *Proc. Natl. Acad. Sci. USA* 87:4761–4765 (1990)], capable of successfully resisting enzymatic degradation [Wade, supra; King, et al., *J. Immunol.* 153:1124–1131 (1994)] and less immunogenic than their all-L-analogues [King, supra].

Figure 1:
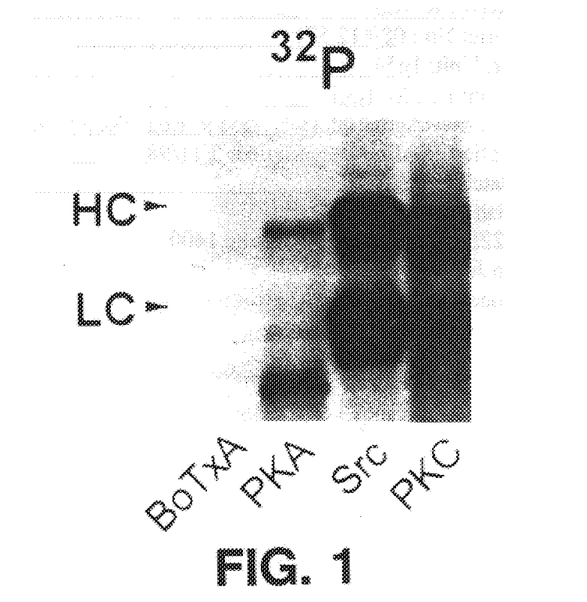
FIG. 1 is an autoradiogram depicting phosphorylation of both the heavy chain (HC) and light chain (LC) of BoTxA by a tyrosine kinase (pp60$^{src}$), measured by incorporation of $^{32}$P into each chain (from [Y-$^{32}$P] ATP).

Although not previously known in the art, BoTx serotypes (particularly, BoTxA, BoTxB and BoTxE) as well as TeTx are substrates for the tyrosine kinase pp60$^{src}$ (FIG. 1 and Example 1). pp60$^{src}$ is a member of the src family of protein kinases that are known to phosphorylate a focal adhesion kinase and induce morphological transformations (e.g., rounding and detachment) in affected cells. pp60$^{src}$ is also abundant in brain synaptic vesicles. pp60$^{src}$ is obtainable by isolation and purification from native sources (e.g., from brain tissue homogenates) or may be purchased commercially from sources such as United States Biochemical of Cleveland, Ohio.

Figure 2:
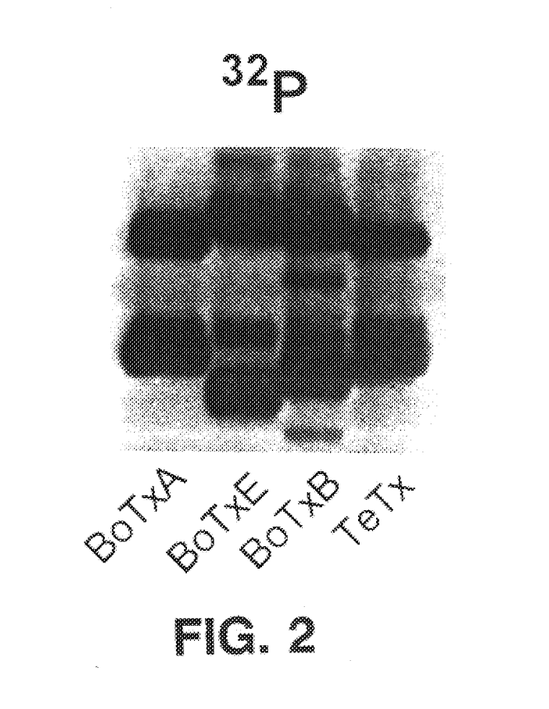
FIG. 2 is an autoradiogram depicting pp60$^{src}$ phosphorylation of BoTxA, BoTxE, BoTxB and TeTx, measured by incorporation of $^{32}$P into each chain (from [Y-$^{32}$P] ATP).
Figure 3:
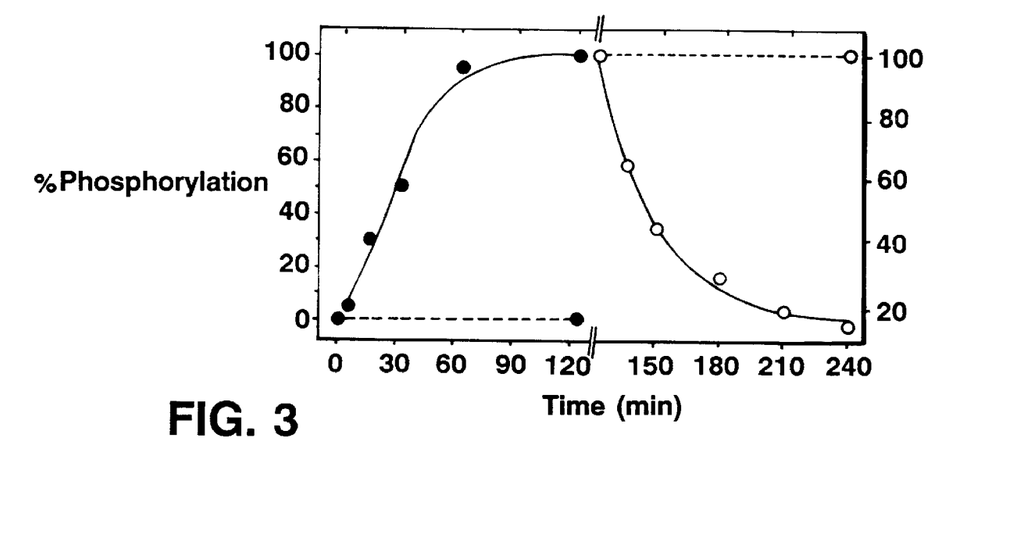
FIG. 3 is a graph depicting the rate of phosphorylation of BoTxA by pp60$^{src}$ (closed circles) and rate of dephosphorylation of pp60$^{src}$ phosphorylated BoTxA in the presence of protein-tyrosine phosphatase 1B (open circles).

Phosphorylation of tyrosine residues in BoTx and TeTx by pp60$^{src}$ is selective (i.e., residues other than tyrosine are not phosphorylated) and occurs throughout both the LC and HC (FIG. 2 and Example 1). For example, half-maximal phosphorylation of the tyrosine residues appears to occur within about 30 minutes on incubation of 250 nanomolar BoTxA starting material with as little as about 3–6 Units of pp60$^{src}$ in buffer (FIG. 3 and Example 1). This ratio of starting material to enzyme (about 250 nanomolar: 3–6 Units) is one in which a minimal amount of enzyme may be used to preserve the enzyme resource and is therefore preferred over effective, but less efficient, protocols in which larger quantities of enzyme are utilized. The reaction is reversible (see, FIG. 3 and Example 1). Similar results are obtainable with another tyrosine kinase recently discovered in neuronal PC12 cells, PYK2 [Lev, et al., *Nature*, 376:737–745 (1995)]. Those of ordinary skill in the art will be readily able to extrapolate the ratios of starting material to enzyme provided herein for production of larger batches of toxin products according to the invention. All ratios of starting material to enzyme in which a toxin product having enhanced proteolytic activity and/or thermal stability (as defined below) is produced are considered to be within the scope of the invention; in this respect, the amount of enzyme utilized will be considered to be a "catalytically effective amount" of enzyme.

Tyrosine phosphorylation is a phenomenon which is a key step in signal transduction pathways mediated by membrane proteins. Thus, other tyrosine kinases (such as other members of the src kinase family) can be expected to be suitable for use as phosphorylating agents in the method of the invention. Surprisingly, however, the enhancement of toxin activity and stability achieved in the invention in specific to toxins in which the tyrosine residues have been modified in vitro to have a negative charge by either covalent attachment of a phosphate or sulphate to the hydroxy group of such residues or substitution of tyrosine residues in the toxin with a negatively charged amino acid (e.g., glutamate or aspartate). Modification of serine or threonine residues in the toxins does not affect the toxins' activity or stability. Thus, serine phosphorylating agents would not be expected to be useful in the method of the invention.

Although enzymatic phosphorylation is preferred for its specificity, phosphorylation may also be produced chemically; i.e., without reliance on a catalytic reaction. Reagents known to be useful in phosphorylating tyrosine residues in proteins include di-t-butyl N,N-diethyl-phosphoriamidite (for phosphorylation in a t-butyl phosphate protection reaction; see, e.g., Perich and Reynolds, *Int.J.Pept.Protein Res.*, 37:572–575 (1991) [incorporated herein by this reference for the purpose of illustrating use of the specified reagent in a conventional peptide synthesis technique] and the discussion above concerning peptide synthesis using the well-known Fmoc/solid phase synthesis technique) and Fmoc-Tyr($PO_3Me_2$)—OH (also applied in the Fmoc/solid phase synthesis technique; id.).

For use in substitution of tyrosine residues with glutamate or aspartate, methods for substituting amino acids in a protein are well-known in the art. For example, in step-wise synthesis of a particular toxin, substitution of tyrosine with aspartate and glutamate may be readily performed by one of ordinary skill in peptide synthesis. Alternatively, using a toxin-encoding polynucleotide as a starting material, a desirable mutation may be produced by site-specific mutagenesis using a conventional polymerase chain reaction (PCR) and a primer pair corresponding to the 3' and 5' regions of the cDNA. A preferred method of mutation-generating PCR amplification is the overlap extension PCR technique described by Ho, et al., *Gene* 77:51–59 (1989), the disclosure of which is incorporated herein by this reference. Generally, this technique accomplishes site-specific mutagenesis of the clone by utilizing a 3' primer to add the mismatched mutating bases (primer B in the Ho article, which is used with the 5' primer A in the first PCR cycle described). Amplification using the A and B primers yields an AB fragment. A second PCR cycle uses a primer (D) from the 3' end of the gene and a 5' mutated primer C complementary to primer B. The resulting amplification product (fragment CD) will overlap the AB fragment. When the AB and CD fragments are denatured, reannealed and amplified using the A and D primers, the resulting fusion product (AD) will contain the full-length cDNA sequence and the desired mutation. Another suitable approach to making single base substitutions or deletions is described by Shaw in U.S. Pat. No. 4,904,584 ("Site-Specific Homogenenous Modification of Polypeptides"), the disclosure of which is incorporated herein by this reference for purposes of illustrating knowledge in the art regarding methods for achieving specific mutations in polynucleotides and polypeptides.

Enhancement of the activity and thermal stability of the toxin products of the inventive process will vary depending on whether the LC, HC or both are phosphorylated. Preferably, both chains will be phosphorylated for maximal enhancement of the toxins' properties, including enhancement of thermal stability (FIG. 7 and Example 3). In this respect, phosphorylation of the LC results in enhancement of the toxins' proteolytic properties (see, FIGS. 4 through 6 and Example 2), while phosphorylation of the HC appears to enhance the toxins' channel gating capabilities by extending the time in which the membrane channels formed by the HC remain open for translocation of the LC into the cytosol (see, FIG. 10 and Example 6). In vivo, phosphorylation of the toxin also appears to potentiate the toxins' activity in blocking the release of neurotransmitters into the synaptic cleft (see, FIG. 8 and Example 5), probably by enhancement of the proteolytic activity of the LC. Given the relatively long-lived activity of BoTx and TeTx observed in vivo (as compared to the relatively short-lived activity of the toxins in vitro), it is probable that in situ phosphorylation of the toxin protects it from intracellular degradation. Thus, in vitro phosphorylation of tyrosine residues likely confers similar protection against toxin degradation both in vitro and in vivo, as evidenced by enhancement of the toxins' in vivo activity and in vitro stability.

Figure 4:
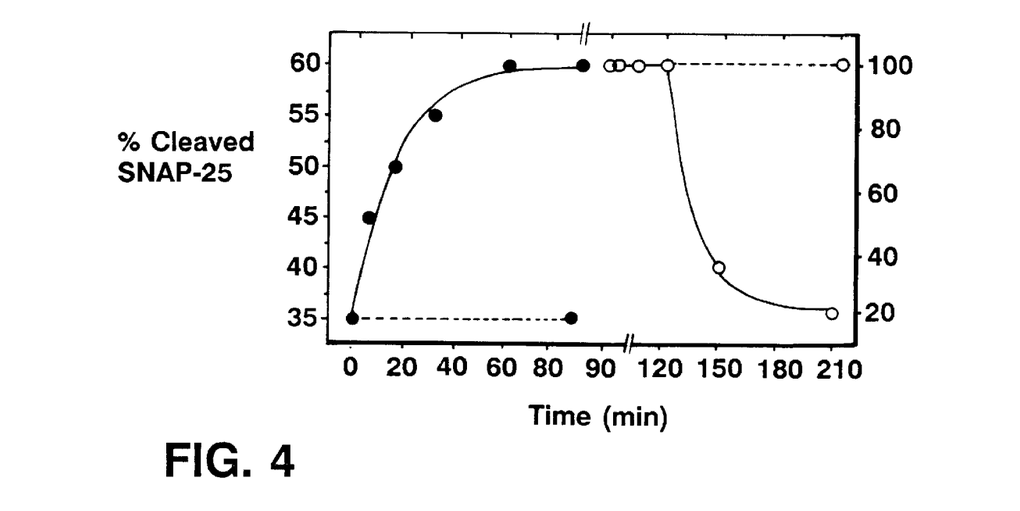
FIG. 4 is a graph depicting the rate of cleavage of SNAP-25 by pp60$^{src}$ phosphorylated BoTxA during phosphorylation (closed circles) and by the same toxin during protein-tyrosine phosphatase 1B dephosphorylation (open circles).

Selective enhancement of either the channel gating or proteolytic activities of the toxin is achievable by phosphorylating only the HC or LC, respectively. Selective phosphorylation of either chain of BoTx or TeTx is performed by cleaving the HC and LC chains for phosphorylation of the tyrosine residues on only the chain to be phosphorylated or by phosphorylating both chains, cleaving the chains and reversing phosphorylation on one chain by applying a dephosphorylating agent such as protein-tyrosine phosphatase 1B (FIG. 4 and Example 2). Compositions containing mixtures of the phosphorylated and unphosphorylated chains are prepared as described below with respect to the fully phosphorylated toxins.

Figure 5A:
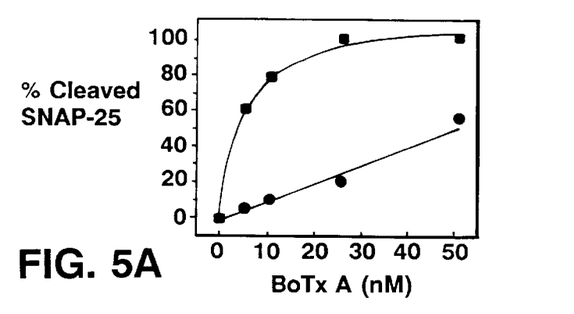
Figure 5B:
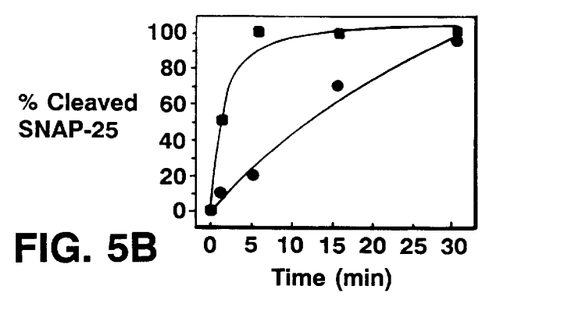
Figure 6A:
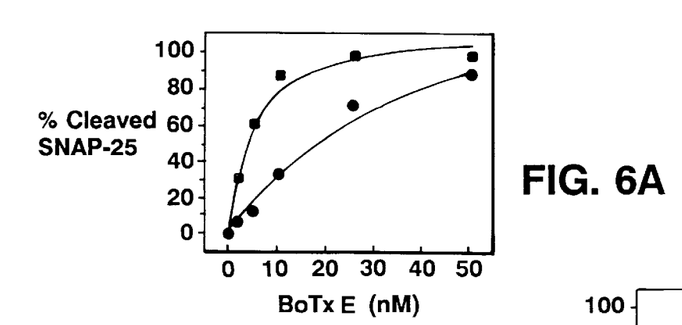
Figure 6B:
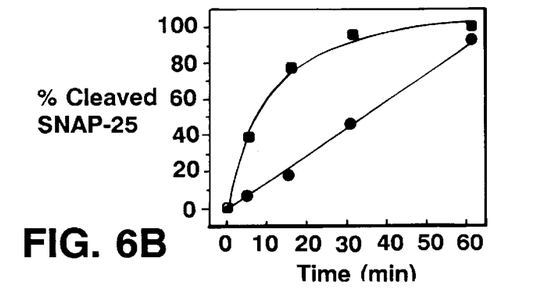
Figure 7:
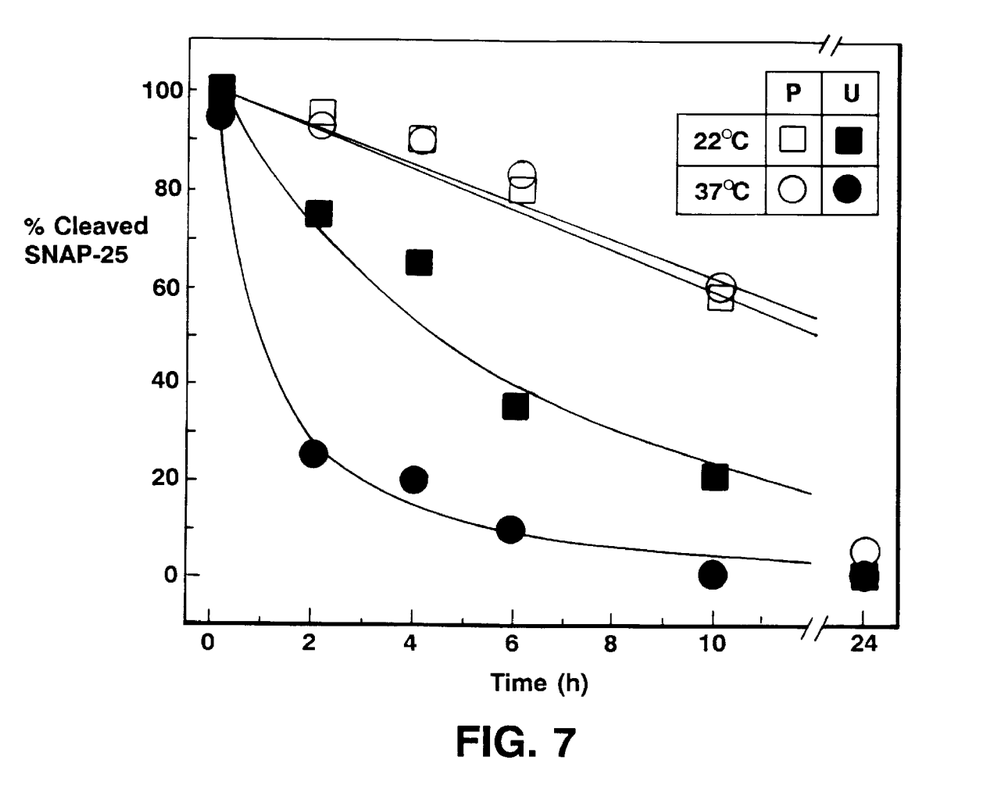
FIG. 7 is a graph depicting the rate of cleavage of SNAP-25 by pp60$^{src}$ phosphorylated BoTxA (open squares and circles) and unphosphorylated BoTxA (closed squares and circles) which were preincubated prior to the cleavage array at either 22° C. (squares) or 37° C. (circles).

Quantitatively phosphorylation of both chains of BoTx or TeTx enhances the proteolytic activity of the toxin by 50% or more compared to the unphosphorylated toxin (FIGS. 4 through 6 and Example 2). However, "enhancement" of toxin proteolytic activity within the meaning of the invention (i.e., as a result of providing a negative charge at the sites of tyrosine residues in the toxin LC) will be considered to occur when the concentration of negatively charged toxin required to produce the same catalytic reaction in vitro in the same time as the unphosphorylated toxin is detectably reduced; e.g., by at least about 10%. Thus, the scope of the invention encompasses phosphorylation of BoTx and TeTx (and the resulting phosphorylated product) using reagents of varying phosphorylating efficiencies, so long as a demonstrable enhancement of the toxin's proteolytic activity as compared to the unphosphorylated toxin occurs.

The thermal stability of the phosphorylated toxin is also enhanced as compared to the unphosphorylated toxin. In particular, BoTx or TeTx having both chains phosphorylated according to the invention can be expected to retain its proteolytic activity in saline at room temperature for at least 5 times longer than the unphosphorylated toxin (FIG. 7 and Example 4). However, "enhancement" of toxin stability within the meaning of the invention (i.e., as a result of providing a negative charge at the sites of tyrosine residues in the toxin) will be considered to occur when retention of the proteolytic activity of the negatively charged toxin in saline at room temperature (37° C.) compared to the unphosphorylated toxin is detectably increased; e.g., by at least about 10%. Thus, the scope of the invention encompasses negatively charged BoTx and TeTx (and the resulting products) using reagents of varying efficiencies, so long as a demonstrable enhancement of the toxin's stability as compared to the unphosphorylated toxin occurs.

Figure 8A:
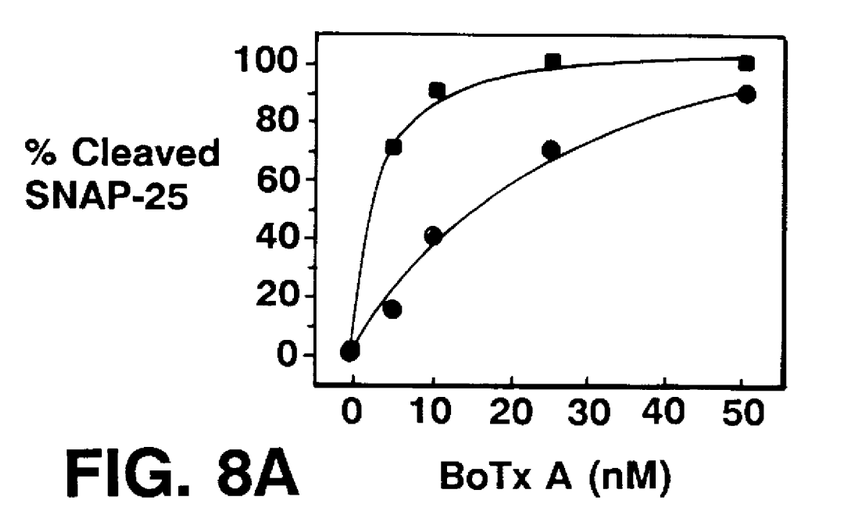
Figure 8B:
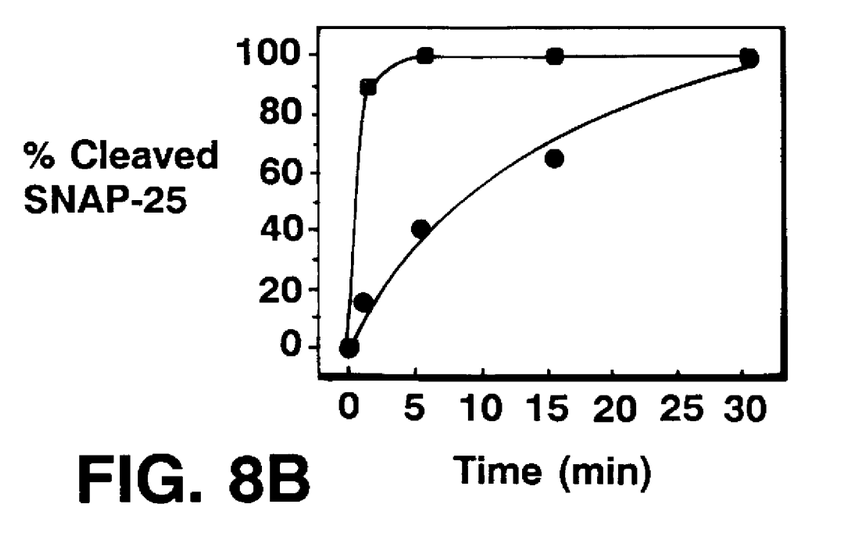

Interestingly, tyrosine phosphorylation of BoTx and TeTx LC has the unexpected effect of restoring proteolytic activity of unphosphorylated toxins which have become inactivated;

e.g., after excessive exposure to moderate heat (see, FIG. 8 and Example 5). Thus, the methods of the invention for preparation of toxins having charge-modified tyrosine residues is useful both in producing pharmaceutically acceptable BoTx and TeTx compositions having enhanced activity as well as restoring activity to conventional unphosphorylated BoTx and TeTx compositions after inactivation.

Assays for use in confirming enhancement of the proteolytic activity and stability of BoTx and TeTx prepared according to the invention are described in the Examples appended hereto. Other techniques for measuring the proteolytic activity and stability of proteins will be well-known to those of ordinary skill in the art and can be readily practiced without undue experimentation (see, e.g., *Methods in Enzymology* (Acad. Press, 1981), the disclosure of which is incorporated herein by reference only to illustrate the state of knowledge in the art concerning techniques for testing and measuring catalytic activity in enzymes). Such assays will be useful not only in determining whether modification of the charge of a particular toxin has enhanced its activity or stability within the meaning of the invention, but will also be useful in determining whether a particular modification of the charge adversely affects the secondary structure and catalytic activity of the toxin to aid in selection and design of pharmaceutically useful negatively charged toxins having charge-modified tyrosine residues according to the invention.

C. Pharmaceutically Acceptable BoTx and TeTx Compositions

Charge-modified BoTx and TeTx compositions of the invention are prepared by mixing the charge-modified toxin having the desired degree of purity with physiologically acceptable carriers. Such carriers will be nontoxic to recipients at the dosages and concentrations employed. Ordinarily, the preparation of such compositions entails combining the particular protein with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

Such compositions may be lyophilized for storage and will be reconstituted according to pharmaceutically acceptable means; i.e., suitably prepared and approved for use in the desired application. A sodium chloride free buffer is preferred for use as a reconstituting agent. Inclusion of bovine or human serum albumin (BSA or HSA) in the composition or reconstituting agent has also been reported to assist in recovery of toxin activity after reconstitution from a lyophilized state (see, e.g., published EPO application No. 0 593 176 A2). Whatever its form, the composition product will be placed into sterile containers (e.g., ampules) for storage and transportation.

Examples illustrating the practice of the invention are set forth below. These examples should not be regarded as limiting the scope of the invention, which is defined by the appended claims. Standard abbreviations (e.g., "ml" for milliliters, "h" for hours) are used throughout the examples.

EXAMPLE I

ENZYMATIC PHOSPHORYLATION OF BoTx AND TeTx TYROSINES BY pp60$^{src}$

Using 250 nanomolar quantities of each toxin, the phosphorylation reaction was conducted in a final volume of 20–40 $\mu$l containing 20 mM MgCl$_2$, 1 mM EGTA, 1 mM DTT, 20 mM Hepes (pH 7.4), 3–6 Units of tyrosine kinase pp60$^{src}$, 0.1 mM ATP and 4 $\mu$Ci [$^{32}$P]-$\gamma$-ATP (3,000 Ci/mmol; Amersham). Reactions proceed at 30° C. at 10 minute intervals for a total of 120 minutes and were terminated by addition of 200 $\mu$M peptide A(pp60$^{+e,dus\ v-src}$ [137–157] [from Peninsula], a specific inhibitor of pp60$^{src}$). For comparison regarding the specificity of tyrosine phosphorylation by pp60$^{src}$, BoTxA was incubated with, separately, serine kinases bovine heart PKA (4 Units, Sigma) and rat brain PKC(20 ng, UBI). For PKC, the phosphorylation buffer was: 20 mM Hepes, pH7.4, 0.1 mM CaCl$_2$, 10 mM MgCl$_2$, 0.25 mg/ml of L-$\alpha$-phosphatidyl-L-serine and 1 mM DTT.

To prepare autoradiograms to detect phosphorylation of each toxin, PKC and PKA, phosphorylated samples were subjected to SDS-PAGE on 12% gels. Gels were stained with Coomassie blue R-250, destained, dried and exposed to Kodak X-Omat AR™ x-ray film. For immunoblots, protein bands were electrotransferred onto nitrocellulose membranes. Bands were visualized using the ECL radiographic system (Amersham). Control samples included samples from which kinases had been omitted. For pp60$^{src}$, an additional control sample was preincubated with peptide A.

Purified BoTxA was strongly phosphorylated by pp60$^{src}$ but not by the serine kinases PKA or PKC. The autoradiograms display incorporation of $^{32}$P into both LC (M$_r$~50 kD) and HC (M$_r$~100 kD) (FIG. 1). pp60$^{src}$ also phosphorylates the HC and LC of BoTxA, BoTxB, BoTxE and TeTx. Autoradiograms display $^{32}$P incorporation into protein (FIG. 2).

As shown in FIG. 3, the phosphorylation reaction between pp60$^{src}$, BoTx and TeTx is reversible. To determine whether the reaction was reversible, dephosphorylation was conducted in vitro in a final volume of 15 $\mu$l containing 0.1 $\mu$M tyrosine-phosphorylated BoTxA and 50 ng PTP-1B-agarose bead conjugate. Reactions proceed at 37° C. for indicated times, and were terminated by centrifugation (14,000 rpm, 1 min) of the PTP-agarose bead conjugate. The extent of BoTxA dephosphorylation was assessed by SDS-PAGE. Controls included omission of PTP or inhibition of PTP with 200 $\mu$M VO$_4$. Phosphorylation of BoTxA was reversed under these conditions.

EXAMPLE II

ENHANCEMENT OF PROTEOLYTIC ACTIVITY IN THE TOXINS OF THE INVENTION

Augmentation of BoTxA protease activity by protein tyrosine phosphorylation. a. Extent of $^{32}$P incorporation into BoTxA HC and LC as function of incubation time in presence of Src. BoTxA was incubated with Src at 30° C. for the indicated time periods, as described in FIG. 1. The band with M$_r$~50 kD corresponds to Src, which is autophosphorylated. b. Tyrosine-phosphorylated BoTxA is enzymatically dephosphorylated by PTP-1B. c. The extent of phosphorylation (a) and dephosphorylation (b) were quantified using an image analyzer. d. Tyrosine phosphorylation of BoTxA is accompanied by augmentation of protease activity. Fluorograms display the mobility change of in vitro translated SNAP-25 due to proteolysis as function of phosphorylation time by Src. Last lane shows a control experiment in which BoTxA was omitted. e.

To measure the proteolytic activity of toxins modified as described in Example I, and to compare that activity to the activity of unmodified toxins, the time required for the modified and unmodified toxins to cleave their respective substrates was tested and compared at various toxin concentrations. To this end, in vitro translation of the cDNA clone coding for SNAP-25 from mouse brain in the presence of [35S]methionine was performed with a transcription-translation-coupled reticulocyte lysate system (Promega). The concentration of modified and unmodified BoTxA or BoTxE incubated with samples of SNAP-25 as shown in FIG. 4 was 10 nM and varied as shown in FIGS. 5 and 6; cleavage reactions were performed at 30° C. In FIG. 4, the unmodified toxin was dephosphorylated as described in Example 1 and the effect of dephosphorylation measured as a function of a decline in proteolytic activity. In FIG. 5, the unmodified toxin was a conventional preparation of BoTxA. In FIG. 6, the unmodified toxin was a conventional preparation of BoTxE.

Samples were analyzed by SDS-PAGE followed by fluorographic detection of $^{35}$S-labeled proteins. The protein band with $M_r$~25 kD is illustrated in cleavage was indicated by a shift to lower $M_r$. Fluorograms were quantified using the NIH program Image 1.57. Two selection windows corresponding to uncleaved SNAP-25 (u) and uncleaved plus cleaved SNAP-25 (u+c) were defined. The integrated density (ID) of each selection was given by ID=N(Mean-Background), where N was the number of pixels in the selection, and the background was the modal gray value (most common pixel value) after smoothing the histogram. The extent of SNAP-25 cleavage (%), is then given by: $(1-ID_u/ID_{u+c} \times 100)$. The resulting data was converted to graph form for ease of comparison.

As shown in FIG. 4, dephosphorylation of BoTxA as described in Example I resulted in a decline of proteolytic activity by a magnitude of about three times (5 minutes cleavage rate for the modified toxin (closed circles) versus about 15 minutes cleavage time for the dephosphorylated toxin (open circles)). As shown in FIG. 5, the modified BoTxA (closed squares) displayed as much as 50% greater proteolytic activity than the unmodified toxin (closed circles; Panel A displays the results obtained as a function of toxin concentration while Panel B displays the results as a function of time). As shown in FIG. 6, the enhancement of activity on the part of modified BoTxE (closed squares) as compared to unmodified BoTxE (closed circles) was similar to the enhancement measured in modified BoTxA (Panel A displays the results as a function of toxin concentration while Panel B displays the results as a function of time).

EXAMPLE III

ENHANCEMENT OF THERMAL STABILITY IN THE TOXINS OF THE INVENTION

Augmentation of BoTx protease activity by protein tyrosine phosphorylation is accompanied by increased thermal stability (FIG. 7). This enhancement in thermal stability was determined by measuring the rates of cleavage of in vitro translated SNAP-25 by tyrosine phosphorylated BoTxA (open squares and circles) or unphosphorylated BoTxA (closed squares and circles) which were preincubated at either 22° C. (squares) or 37° (circles) prior to the cleavage assay. The assay was conducted at 30° C. at a fixed toxin concentration of 20 nM.

EXAMPLE IV

RESTORATION OF ACTIVITY TO THERMALLY INACTIVATED TOXINS BY MODIFICATION OF THE TOXIN ACCORDING TO THE INVENTION

To determine whether activity could be restored to thermally inactivated toxins by modifying the toxins according to the invention, unmodified BoTxA was thermally inactivated to a loss of approximately 90% of its original activity by exposure to room temperature (37° C.) for 6 hours. One-half of the inactivated materials were tyrosine phosphorylated as described in Example I. The modified and unmodified toxin samples were incubated with SNAP-25 as described in Example II. As shown in FIG. 8, the modified toxin displayed proteolytic activity similar in magnitude to the modified toxins described in Example III (closed squares) while the unmodified toxin displayed little proteolytic activity (closed circles).

EXAMPLE V

INHIBITION OF NEUROTRANSMITTER RELEASE: PREDICTED ENHANCEMENT OF INHIBITORY ACTIVITY IN THE TOXINS OF THE INVENTION

Intracellular tyrosine phosphorylation of BoTxA LC in NGF-differentiated PC12 cells is associated with potentiation of neurotransmitter release blockade. To predict the effect of modification of the toxins of the invention on their inhibitory activity with respect to neurotransmitter release, pheochromocytoma (PC12) cells were propagated in RPMI 1640 medium, supplemented with 10% donor horse serum-5% bovine fetal serum, at 37° C. in a humidified incubator with 5% CO2. For NGF (nerve growth factor) cellular differentiation (50 ng/ml, for 4 days), PC12 cells were plated at a density of $10^6$ cells/ml on 75 cm$^2$ culture dishes with rat tail collagen.

Cells were incubated with modified or unmodified BoTxA dissolved in PBS for 12 h. Cells were stimulated with PBS supplemented with indicated additives, washed with cold PBS, lysed with cold radioimmunoprecipitation (RIPA) buffer (20 mM Tris-HCl pH 7.4, 200 mM NaCl, 1 mM NaF, 1 µg/ml pepstatine A and 1 mM phenylmethylsulfluoride), incubated and shaken at 4° C. Insoluble material was removed by centrifugation at 10,000×g for 30 min at 4° C. Soluble material was analyzed by immunoblot or used for immunoprecipitation. Tyrosine-phosphorylated proteins were immunoprecipitated with an antiphosphotyrosine monoclonal antibody. Immunocomplexes were captured with agarose-conjugated protein G (Pierce), and analyzed by SDS-PAGE and immunoblotting. Bands were visualized using the ECL system (Amersham) to confirm incorporation of the toxins into the cells.

Figure 9:
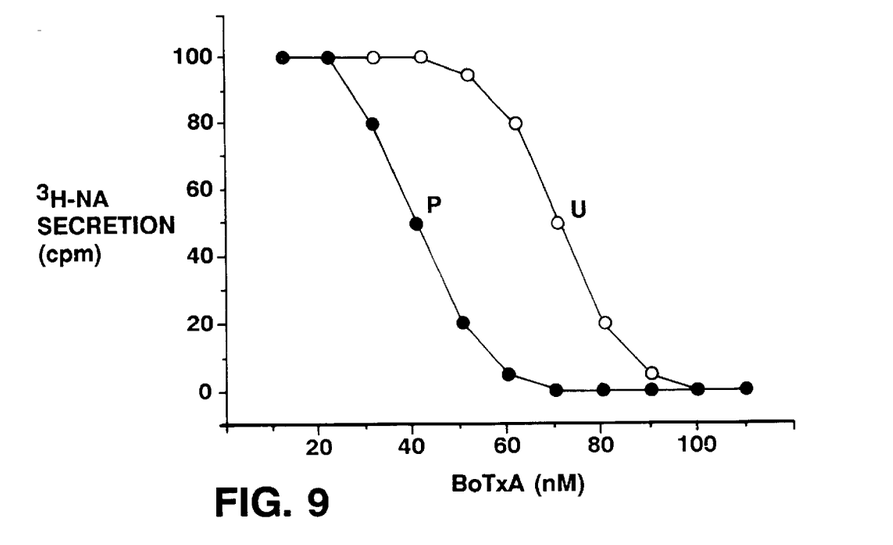
FIG. 9 is a graph depicting the predicted extent of inhibition of [$^3$H]-noradrenaline neurotransmitter from neuronal (PC12) cells on incubation of the cells with pp60$^{src}$ phosphorylated BoTxE (closed circles) or unphosphorylated BoTxA (open circles).

The cells were stimulated with nerve growth factor and the extent of [$^3$H]-labeled noradrenaline neurotransmitter release from the cells measured. While the results of these experiments are preliminary, as shown in FIG. 9, release of noradrenaline is predicted by the data to be inhibited to a substantially greater degree in the cells treated with modified BoTxA (closed circles) as compared to the cells treated with unmodified BoTxA (open circles).

EXAMPLE VI

ENHANCEMENT OF CHANNEL GATING ACTIVITY IN THE TOXINS OF THE INVENTION

Figure 10:
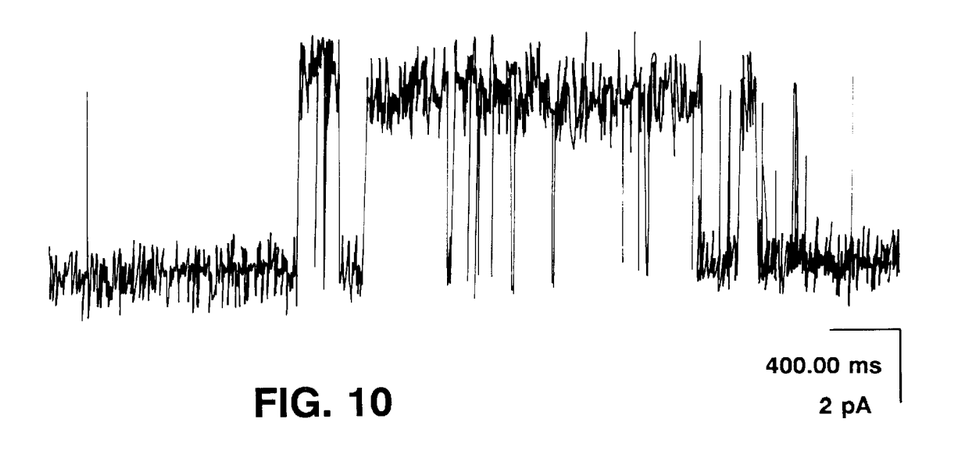
FIG. 10 depicts the single channel currents of pp60$^{src}$ p-phosphorylated BoTxA HC reconstituted in lipid bilayer membranes.

To determine the non-channel activity of the toxins of the invention, modified BoTxA were reconstituted into lipid bilayer membranes. As shown in FIG. 10, the channel formed by the modified toxin exhibits a high probability of being in the open state (top current level). This indicates augmentation of the ion channel activity of the modified toxin HC in comparison to unmodified toxin.

The invention having been fully described, modifications thereof will become apparent to those of ordinary skill in the art. All such modifications of the invention are to be considered to be within the scope of the appended claims.

What is claimed is:

1. A Clostridium neurotoxin having tyrosine residues phosphorylated to have a negative charge, wherein the proteolytic activity and thermal stability of the neurotoxin are enhanced as compared to Clostridium neurotoxins in which negatively charged tyrosine residues are absent.

2. The neurotoxin according to claim 1 wherein the neurotoxin is a *Clostridium botulinum* neurotoxin.

3. The neurotoxin according to claim 2 wherein the neurotoxin is botulinum toxin A, botulinum toxin B, or botulinum toxin E.

4. The neurotoxin according to claim 1 wherein the neurotoxin is a *Clostridium tetani* neurotoxin.

5. A pharmaceutical composition comprising a Clostridium neurotoxin having tyrosine residues phosphorylated to have a negative charge, and a pharmaceutically acceptable carrier, wherein the proteolytic activity and stability of the neurotoxin are enhanced as compared to Clostridium neurotoxins in which negatively charged tyrosine residues are absent.

6. The pharmaceutical composition according to claim 5 wherein the neurotoxin is a *Clostridium botulinum* neurotoxin.

7. The pharmaceutical composition according to claim 6 wherein the neurotoxin is botulinum toxin A, botulinum toxin B or botulinum toxin E.

8. The pharmaceutical composition according to claim 5 wherein the neurotoxin is a *Clostridium tetani* neurotoxin.

9. A Clostridium neurotoxin wherein tyrosine residues therein are sulfated to have a negative charge, wherein further the proteolytic activity and thermal stability of the neurotoxin are enhanced as compared to Clostridium neurotoxins in which negatively charged tyrosine residues are absent.

10. The neurotoxin according to claim 9 wherein the neurotoxin is a *Clostridium botulinum* neurotoxin.

11. The neurotoxin according to claim 10 wherein the neurotoxin is botulinum toxin A, botulinum toxin B, or botulinum toxin E.

12. The neurotoxin according to claim 9 wherein the neurotoxin is a *Clostridium tetani* neurotoxin.

13. A pharmaceutical composition comprising a Clostridium neurotoxin wherein tyrosine residues therein are sulfated to have a negative charge, and a pharmaceutically acceptable carrier, wherein further the proteolytic activity and stability of the neurotoxin are enhanced as compared to Clostridium neurotoxins in which negatively charged tyrosine residues are absent.

14. The pharmaceutical composition according to claim 13 wherein the neurotoxin is a *Clostridium botulinum* neurotoxin.

15. The pharmaceutical composition according to claim 14 wherein the neurotoxin is botulinum toxin A, botulinum toxin B or botulinum toxin E.

16. The pharmaceutical composition according to claim 13 wherein the neurotoxin is a *Clostridium tetani* neurotoxin.

* * * * *